United States Patent
Kosti

(10) Patent No.: US 6,759,030 B2
(45) Date of Patent: Jul. 6, 2004

(54) BLEACH STABLE TOOTHPASTE

(75) Inventor: Carl M. Kosti, 8513 Breezewood Ct. #207, West Chester, OH (US) 45069

(73) Assignee: Carl M. Kosti, Mason, OH (US)

( * ) Notice: Subject to any disclaimer, the term of this patent is extended or adjusted under 35 U.S.C. 154(b) by 0 days.

(21) Appl. No.: 10/103,222

(22) Filed: Mar. 21, 2002

(65) Prior Publication Data

US 2003/0180229 A1 Sep. 25, 2003

(51) Int. Cl.$^7$ ................................. A61K 7/20
(52) U.S. Cl. ..................... 424/53; 433/215; 433/216
(58) Field of Search .................... 424/53; 433/215, 433/216

(56) References Cited

U.S. PATENT DOCUMENTS

| | | | |
|---|---|---|---|
| 4,102,992 A | * 7/1978 | Davis | 424/49 |
| 4,927,627 A | * 5/1990 | Schrader et al. | 424/62 |
| 5,238,992 A | * 8/1993 | Outubuddin | 524/710 |
| 5,472,954 A | * 12/1995 | Loftsson | 514/58 |
| 5,759,989 A | * 6/1998 | Scialla et al. | 510/500 |
| 5,879,584 A | * 3/1999 | Bianchetti et al. | 252/186.23 |
| 5,880,079 A | * 3/1999 | Polotti et al. | 510/309 |
| 5,997,585 A | * 12/1999 | Scialla et al. | |
| 6,083,489 A | * 7/2000 | Fischer et al. | 424/49 |
| 6,221,395 B1 | * 4/2001 | Maggi et al. | 424/475 |

* cited by examiner

Primary Examiner—Frederick Krass
(74) Attorney, Agent, or Firm—R. William Graham

(57) ABSTRACT

This invention relates to novel and improved bleach-stable compositions and processes and methods of making such compositions. More particularly, the invention relates to providing improved dental compositions comprising an effective amount of a discontinuous phase consisting of one or more hydrophobic, inert, bleach-stable abrasive agents that are polymers, copolymers and crosspolymers of granular nature of about between 2 microns and 150 microns particle size, present in the operative range of about 10% and 75% with respect to the total weight of the composition, said abrasive agents are dispersed or otherwise distributed in a continuous phase comprising one or more bleaching actives emulsed in an inclusion complex polymer (ICP) of delayed water and saliva solubility said emulsified bleaching active being capable of forming a long lasting bleaching film on tooth surfaces and being present in the operative range of about 0.5% and 55% with respect to the total weight of the composition, said composition being stable for a long periods when contained in a single chamber, such as toothpaste tube, and the said emulsed bleaching active being activated only when extruded from the container and exposed to the salivary enzymes. The composition may contain other formulating agents.

23 Claims, 1 Drawing Sheet

BLEACH STABLE TOOTHPASTE

BACKGROUND OF THE INVENTION

I. Field of the Invention

The destruction of teeth by dental caries and the loss of their support through inflammatory periodontal disease is related to the activity of microbial plaque. Although differing in particulars, the relationships are essentially identical: pathogenic microorganisms become attached to a tooth, take in nutrients and liberate chemicals that are injurious to the target site, whether tooth, periodontium, or both. The attachment of organisms can be effected by growth in the sheltered areas such as pits, fissures and faults of teeth, by self-produced adherence and colonization, such as in plaque formation, or by a combination of processes. Given sufficient nutrients and time to form toxic substances, the microorganisms will produce caries and periodontal lesions at susceptible sites.

II. Description of the Prior Art

The problem of preventing caries and inflammatory periodontal disease has been approached experimentally by attempting to interfere with plaque formation and activity and by altering tooth surfaces. Attempts to change surface characteristics of teeth to prevent colonization of microorganisms remain a problem. Alterations in the chemical rather than physical characteristics of the target site have been achieved to some extent by the exposure of the tooth surfaces to fluoride ions made available in water supply, dietary supplements, dentifrices, mouthwashes, topically applied solutions and gels, and respective materials. Unfortunately, no such simple and effective agent is available to alter the soft tissues. The most successful control of plaque related to dental caries and periodontal disease has been professional mechanical removal.

In recent past, particularly since the advances of bleaching procedures of tooth surfaces either by the in-office procedure or home treatment procedure, it is a well accepted method to mechanically remove the oral plaque formulations prior to bleaching. Voluminous studies have been conducted which indicate that plaque formulation is detrimental to the bleaching process due to the inability of the bleaching actives to penetrate easily the plaque lipoid formation and affect cosmetic effect on the tooth surfaces.

In rather simple terms, dental plaque has been described as a tenacious, soft deposit consisting chiefly of bacteria and bacterial products. More precisely, plague includes specific types of bacterial colonies surrounded by gel-like intercellular substance derived chiefly from the bacteria themselves, but also containing components from saliva and crevicular fluids, leucocites and epithelial cells. The microflora of the plaque is water insoluble and degrades the bleaching actives rapidly and must be mechanically removed prior to bleaching.

Recent bacteriological and biochemical studies of oral plaque suggest that plaque should be considered a liposome. Liposomes are self-assembled, self-closed colloidal particles in which their membrane is composed from a lipid bilayer and encapsulates a fraction of the solvent in which they are suspended. Because liposomes can entrap hydrophilic molecules into their interior, usually fermentable bacterial acids, and hydrophobic molecules into their lipophilic membrane, they have the capacity to absorb these molecules as well. Plaque liposomes, in particular the hydrophilic fermentable acids in the inner structure of the molecule, in presence of peroxidase and catalase will interact with polypeptide chains and diminish, if not totally destroy, the efficacy of the enzymes to interact with hydrogen peroxide to generate oxygen.

Hydrogen peroxide is an amphiphilic compound. It contains hydrophilic and lipophilic molecules which can readily be neutralized by the bacterial acids, usually acidic and lactic acids, that are freely produced by the polysaccharides of plaque. Therefore, it is essential that the oral cavity be relatively free of plaque accumulations prior to bleaching and whitening procedures.

The bleaching of teeth and removal of plaque has been the home care procedure most widely recommended to promote oral cleanliness and aesthetic appearance. Its basic purpose is to remove oral accumulation of plaque and debris and thereby assist in the bleaching process. Bleaching agents, such as hydrogen peroxide, carbamide peroxide, calcium peroxide, perborates and peracids, for example, are readily degraded in presence of organic matter or in the presence of abrasives that contain salts of metals, particularly transient metals. The composition of the plaque appears to be lipoidal in character and the interfacial tension between it and the tooth surfaces is quite high. As a result, in absence of an abrasive to mechanically remove the plaque accumulation, an excess amount of bleaching actives is necessary to effect bleaching. However, when hydrogen peroxide is emulsed in inclusion complex substances they have reduced water and saliva and water solubility, the amount of bleaching actives can be significantly reduced; said composition being stable over a long period of time even when contained in a single chamber, such as toothpaste tube. The oral compositions of the present invention may contain additional formulating agents such as topical local anesthetics, sweeteners, preservatives, thickeners and emulsifiers, fluoride compounds, pH adjusting compounds, humectants, flavors, colorants, surfactants, alcohols and water.

SUMMARY OF THE INVENTION

It is an object of the present invention to provide improved toothpaste bleaching composition for use in the oral cavity with improved stability.

It is also an object of the present invention to provide improved bleaching compositions for use in the oral cavity that contains inclusion complex polymers and copolymers to retard for a relatively short period of time the solubility of the bleaching actives contained within the composition and forming long lasting bleaching film on the tooth surface.

It is another object of the present invention to provide improved bleaching compositions of the type stated wherein the oral cavity is rendered relatively free of plaque accumulations prior to activation of bleaching agents contained therein.

It is yet another object of the present invention to provide oral compositions of the type stated wherein the abrasive agent is an inert bleach-stable polymer, copolymer or crosspolymer.

It is still yet another object of the present invention to provide oral compositions of the type stated wherein the bleaching actives and the abrasive agents are capable of co-containment.

It is further an object of the present invention to provide oral composition of the type stated wherein one of the bleaching active is carbamide peroxide and the other is hydrogen peroxide.

It is further yet an object of the present invention to provide an improved stable bleaching composition of the type stated wherein the carbamide peroxide composition is separated in the form of stripe or stripes from the balance of the composition comprising hydrogen peroxide actives dispersed in a main phase containing formulating aids.

It is still further an object of the present invention to provide an improved bleach stable dental composition useful in the treatment of gingivitis and in the prevention of periodontal disease.

It still yet another object of the present invention to provide an improved bleach stable dental composition of the type stated in the control of dental malodors.

It is still further yet another object of the present invention to provide an improved bleach-stable dental composition of the type stated and formed into a solid tablet that can be employed in the treatment of post-extraction necrotic socket (dry socket) to prevent pain associated with subsequent infection.

In utilizing the oral composition wherein the bleach-stable abrasive agents and the bleaching actives are formulated to be packaged in one chamber, or container, a desired amount of the composition is disposed on a toothbrush, or any other instrument, and topically applied on selected tooth surfaces and by the mechanical action of the tooth bristles the abrasive agents effectively and quickly remove the plaque accumulations from the tooth surfaces to allow the slightly action retarded bleaching agents, which are contemporaneously acted upon by the salivary enzymes catalase and peroxydase to generate free oxygen to then diffuses into the plaque-free enamel easily and quickly where it releases free radicals with unpaired electrons. These free radicals oxidize the organic matter, which causes many stains, to create lighter intermediates by cleaving carbon ring structures. As the bleaching process proceeds, double bonds in the lighter intermediates are broken and the material reaches its saturation point. Bleaching slows down dramatically when there are no longer double bonds available and the bleaching process ceases before the carbon backbones of protein are attacked which may result in the loss of enamel matrix.

The oral compositions of the present invention may comprise bleaching actives that have quick onset of activity, such as hydrogen peroxide and carbamide peroxide, that are relatively inexpensive and readily available.

In summary, peroxygens, in particular hydrogen peroxide and carbamide peroxide, when utilized as an agent for whitening and bleaching of teeth, and in presence of significant plaque accumulation, the plaque microflora releases a large amounts of acids to react with peroxidase and catalase to degrade their ability to interact with hydrogen peroxide to generate oxygen. The reduced amount of generated oxygen being lipophilic, will be attracted by the lipid plaque by the interfacial tension that exists between the two liposomes and thus prevents its diffusion into the enamel rods in search of the double-bonded stains.

Accordingly, the present invention is directed to a bleaching oral composition comprising (a) a continuous phase of water soluble, water miscible, hydrophilic composition containing an effective amount of one or more bleaching actives present in the operative range of about 0.5 percent and 55 percent with respect to the total weight of the composition, distributed, dissolved or otherwise emulsed in a composition containing inclusive complexes that are slowly water soluble polymers or copolymers in addition to sweeteners, flavors, topical anesthetics, humectants, alcohols, and other formulating adentaes and (b) uniformly dispersed throughout said continuous phase; and (b) a discontinuous phase of an effective amount of one or more bleach-stable inert polymer, copolymer and crosspolymer abrasive agents present in the operative range of about 10 percent and 75 percent with respect to the total weight of the composition.

When topically applied to tooth surfaces, the inclusion complex polymers and copolymers retard the activity of the bleaching agents sufficiently to allow the abrasive agents by mechanical action remove the plaque and pellicles from enamel surfaces thus allow for easier diffusion of the bleaching agents into the plaque and pellicle-free enamel thus allowing the bleaching active to effectively whiten the tooth surfaces. The composition of the present invention may contain additional formulating agents such as sweeteners, 0.5% to 10%; flavors, 0.5% to 15%; preservatives, 0.5% to 15%; topical anesthetics, 0.0% to 15%; thickening and emulsifying agents, 1.0% to 25%; humectants, 0.5% to 45%; buffers, to adjust the pH of the composition between 5.5 to 8.5; alcohols, 0.0% to 25%; colors, 0.0% to 15%; solvents (other than water), 0.0% to 50%; fluoride compounds, 0.0% to 5%, and water 10% to 80%.

Other objects and advantages of the present invention will be apparent to those skilled in the art on reading the following disclosure, and therefore, the invention includes the new and novel compositions and processes of making and using compositions herein illustrated.

DESCRIPTION OF THE PREFERRED EMBODIMENT

Figure 1:
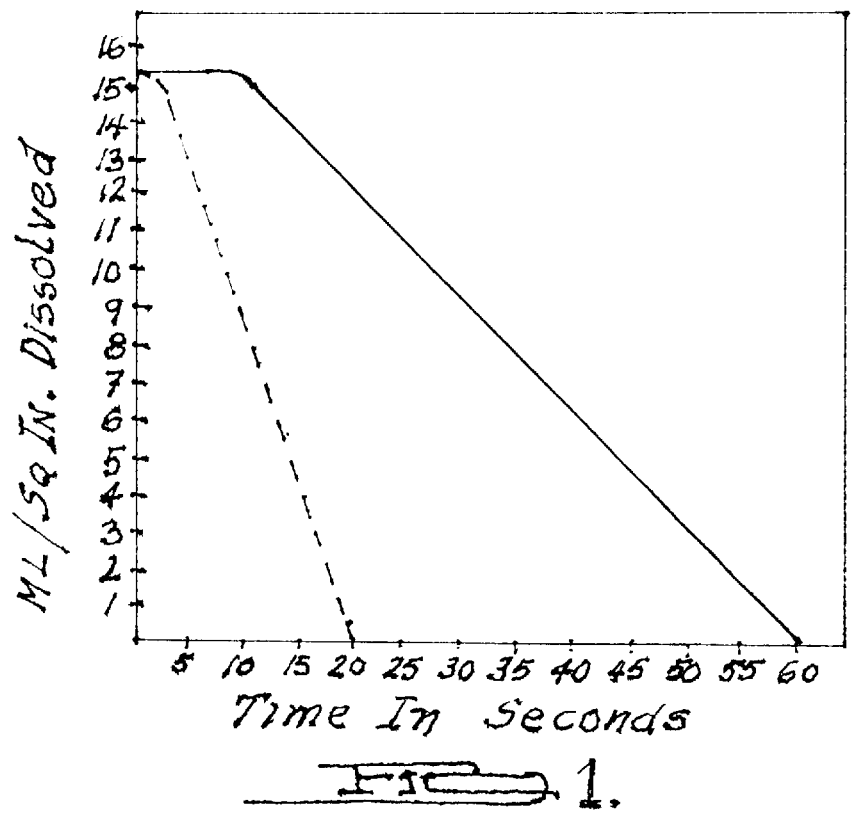
FIG. 1 depicts a graph showing the dissolution of the composition of the present invention.

The bleaching actives of the present oral compositions are selected from those peroxygen that are physiologically and pharmacologically tolerable with reference to the particular oral utility of the invention and preferably should be water soluble and water miscible. They can be solid, liquid or gel and can be dispersed, emulsed, suspended, dissolved or otherwise distributed in the bleaching phase. It has been found in connection with the present invention that the most suitable bleaching substances are actives selected from a group consisting of (a) peroxygens, such as hydrogen peroxide, carbamide peroxide, sodium peroxide, sodium carbonate peroxide, stabilized chlorine dioxide, sodium perborate, sodium perborate monohydrate, sodium percarbonate wherein carbonate peroxyhydrate is magnesium peroxide; (b) peracids, such as magnesium monoperoxyphthalate, diperoxydodecanedioic acid, peroxydiphosphate, etc; (c) enzymes such as oxydoreductaze, lysozyme, etc. and similar organic and inorganic compounds which gererate oxygen when exposed to acids, bases, metals, organic mater and specific enzymes.

The most preferred peroxygens of the group are hydrogen peroxide and carbamide peroxide. They may be present in an effective amount in the range from about 0.5% and 55% with respect to the total weight of the composition. The percent concentration may vary depending upon its activity. For hydrogen peroxide, for example, the preferred concentration in the present invention is between 1% and 45% with the range from about 2% and 25% being most preferred. In the case of carbamide peroxide the preferred concentration is 3% to 55% with the range from about 5% 45% being most preferred.

The bleaching oral compositions of the present invention are best made by dispersing and emulsifying a selected amount of one or more harmless peroxygens in an equally harmless slightly water soluble, hydrophilic substance that can be inclusion complex polymers and/or copolymers and mixing said composition into a composition consisting of sweetening agents, flavors, humectants, alcohols, topical anesthetics and other formulating agents until a continuous homogeneous mixtures is obtained. Throughout this composition and effective amount of one or more bleach-stable, inert solid abrasive agents that are polymers, copolymers and crosspolymers are homogeneously dispersed to form a discontinuous phase. The two phases, the continuous bleaching phase and the discontinuous abrasive phase are mixed and the resultant toothpaste or gel formulation is then packaged into a single dispensing container. Favorable results are obtained when the bleaching actives are premixed separately in liquid composition comprising only water and emulsifying inclusion complex polymer and copolymer agents prior to being added to the continuous phase comprising all other formulating addendae. However, the bleaching and the abrasive agents may be added directly to the continuous phase without pre-mixing in the thickening and emulsifying agents. When the actives are added directly without pre-mixing, the admixture then must be blended for a much longer period of time to produce a toothpaste of homogeneous distribution throughout. There is a possibility that the bleaching actives may form isolated islands in the continuous phase unless mixed completely.

The bleaching oral compositions of the present invention are effectively used by topically applying the same to the teeth with a toothbrush or other suitable instrument and mechanically remove the plaque formation and pellicle layer from the enamel surfaces to allow the bleaching actives that are now reduced to water and oxygen by the activity of the salivary enzymes catalase and peroxydase and permit the free oxygen to penetrate the plaque-free surfaces into the enamel rods and dentinal tubules to effect whitening of the teeth initially for selective staining the plaque accumulations on the tooth surfaces. The procedure may be repeated daily for about 2 minutes to assure acceptable whitening.

The abrasives of the present oral compositions are selected from those polymers, copolymers and crosspolymers that do not undergo the chemical reaction of polymerization in the presence of any of the oral composition ingredients and are physiologically and pharmacologically tolerable with reference to the particular utility of the invention and must be water insoluble and water immiscible. They are preferably granular or crystalline and of sufficient particle size to provide mild abrasive action of the tooth surfaces to remove plaque accumulations.

The polymers, copolymers and crosspolymers comprise a member of a group consisting of substances which are synthetic resins or other substances made by a process, synthesis or similar artifice, extracted, isolated, or otherwise derived, with or without intermediate or final change of identity, from vegetable, animal, mineral, or other source that, when added or applied to tooth surfaces or any other surface or substance, are capable, alone or through reaction with other substances, of imparting plaque-free surface thereto. There are a significant number of polymers and copolymers that are useful as abrasives in the present invention.

Suitable abrasives, for example, are selected from a group consisting of polyacrylates, such as polymethyl methacrylate; methyl methacrylate crosspolymer (methylmethacrylate-ethyleneglycoldimethylacrylate crosspolymer); copolymers of acrylate and methacrylate with quaternary ammonium group as functional group, ethylacrylate methacrylate copolymer with a neutral ester group; polycellulose acetate and polycellulose nitrate; poly(phenyl-formeldhyde); polyvinyls; polytetrafluoroethylene (Teflon); polyethylene powder (plastic solid ethene homopolymer of milky transparency; PVP/dimethylaminoethylmethacrylate/polycarbamyl polyglycol ester(Pecogel GC-1110) The abrasives are present in effective amount operative range from about 10% and 75% with respect to the total weight of the composition.

The most suitable hydrophobic, bleach-stable abrasives of the present invention are methyl methacrylate, polymethyl methacrylate, methyl methacrylate crosspolymer, polytetrafluoroethylene, polyethylene powder, polycellulose acetate, polycellulose nitrate, Nylon-12 and Styrene/DVB Copolymer (Crosslinked Polystyrene) and mixtures thereof.

Examples of some inclusion complex polymers and copolymers useful in the present invention to slightly retard the solublity of the bleaching actives are a group of substances that are water soluble, bleach-stable emulsifiers comprising a group consisting of anionics; amphoterics; alkanolamides, amineoxides; cationics; nonionics such as emulsifying waxes, glycerol and glycol esters, ethoxylated fatty esters, block polyols, ethoxylated alcohols, sorbitan esters, ethoxylated sorbitan esters; silicons such as organosilicones, silicone fluids, volatile silicones; emollients and moisturizers such as polyethylene glycols, polypropylene glycols, and acrylic emulsions. Preferred emulsifiers are acrylic emulsions such as ammonium styrene/acrylates copolymer/bytalene glycol/sodium lauryl sulfate, acrylates/ammonium methacrylate copolymers, polyethacrylate, and nonionics such as block polyols like poloxamer, and acrylates such as carbopol; modified polyethylene glycol/polypropylene glycol; and vinyl pyrrolodone/acrylic acid copolymer. The emulsifier may be present in an effective amount of about 0.5% and 45% with respect to the total weight of the composition.

In addition components specified herein will generally have additives performing specific desired functions such as sweetening agents, flavoring agents, preservatives, topical anesthetics, humectants, fluoride yielding compounds, alkalis, foaming agents, antimicrobial agents and water.

Examples of some topical anesthetics suitable in the present invention are selected from a group consisting of ethyl 4-aminobenzoate (Benzocain), chlorobutanol, lidocain, butacaine sulfate, tetracaine hydrochloride, dyclonine hydrochloride, cocaine hydrochloride and mixtures thereof. The topical anesthetic may be present in an effective amount of about 0.0% and 15% with respect to the total weight of the composition.

Examples of some of the sweetening agent suitable to be employed in the present invention are selected from a group consisting of sodium saccharine, xylitol, sorbitol, and mixtures thereof and they may be present in an effective amount of about 0.05% and 2.5% with respect to the total weight of the composition.

Examples of flavoring agents suitable to be used in the present invention are substances selected fro a group consisting of essential oils such as anise oil, clove oil, peppermint oil, spearmint oil, menthol, methyl salicylate, etc.; natural and synthetic substances such as blackberry, strawberry, chocolate, vanilla, cherry, grape, lime, lemon, mint, etc and mixtures thereof an they may be present in an effective amount in the operative range from about between 0.5% and 20% with respect to the total weight of the composition.

Examples of preservatives suitable in the present invention may be selected from a group consisting of sodium benzoate, methyl paraben, propyl paraben, phenyl mercuric nitrate, sodium bisulfite, disodium calcium EDTA, chlorobutanol, etc. and mixtures thereof and they may be present in the operative effective range of about between 0.5% and 5.0% with respect to the total weight of the composition.

Examples of some humectants or moisture retaining agents suitable in the present invention are glycerol, sorbitol, propylene glycol, polyethylene glycol in the series fro 10 and up, polysorbate, diethylene glycol monoethyl ether, polyethylene sorbitan monolaurate, etc. and mixtures thereof and they may be present in the operative range of about 0.50% and 45% with respect to the total weight of the composition.

Examples of fluoride yielding compounds suitable in the present invention are sodium fluoride, stannous fluoride, hydrogen fluoride, sodium monofluorophosphate, calcium fluoride. and mixtures thereof in concentration of about between 0.00% and 5.00% with respect to the total weight of the composition.

Examples of foaming and surfactant agents suitable in the present invention are selected from a group consisting of carbopol, block copolymers, dioctyl sodium sulfosuccinate, sodium sodium lauryl sulfoacetate, sodium lauryl sulfate, sulfocolaurate, sodium lauryl sarcocinate, sodium coconut monoglyceride, sodium tetradecyl sulfate, etc. and mixtures thereof and may be present in the operative range from about between 0.05% and 10.00%.

Examples of pH adjusting agents suitable in the present invention consist of alkalis such as sodium hydroxide, ammonium hydroxide, monosodium phosphate, dibasic sodium phosphate, trisodium phosphate, sodium bicarbonate and similar compounds that are capable of raising the pH of the composition between 5.5 and 14.

Examples of antimicrobial agents useful in the oral compositions of the present invention may be selected from a group consisting of alcohols, formaldehyde preparations and compounds which liberate formaldehydes, hypochloride substances, iodine preparations, mercury preparations and phenolic compounds such as halogenated diphenyl ethers, halogenated salicylanilides, benzoic esters, halogenated carbanilides, phenol and its homologs, mono- and poly-alkyl and aralkyl halophenols, resorcinol and its derivatives, bisphenolic compounds and mixtures thereof. Antimicrobials may be present in the operative range between about 0.00% and 10.00% with respect to the total weight of the composition.

The oral compositions of the present invention may contain water present in the operative range from about 0.5% and 82% with respect to the total weight of the composition.

A study was conducted to evaluate the efficacy of the [IPC(SI)] in the influence of delaying the solubility of the emulsed carbamide (urea) peroxide in the toothpaste composition to allow the abrasive agents to remove the plaque formation on enamel surfaces prior to the bleaching activity. In the study model compositions containing carbamide peroxide emulsed in [ICP(SI)] and compare them to another set of carbamide peroxide emulsed in common toothpaste thickening and emulsifying agents presently employed. To demonstrate proof-of-concept and to simulate in vivo trial saliva was obtained from human subjects. Twenty 50 mL beakers were used wherein 25 ml of the saliva and plurality of emulsified carbamide peroxide in the amount to produce viscosities of about 50,000 and 150,000 centipoises were added. The titrating solution was prepared with potassium permanganate in a sulfuric acid solution.

The titrating solution was added to each beaker dropwise in 0.5 ml increments until color change occurred. A stopwatch in 1/100th of a second was used to measure the speed of color change and the result recorded. The calculation of the amount of carbamide peroxide generated was calculated by each 1 ml of potassium permanganate solution (0.02 moles/liter) is equivalent to 1.7 mg of hydrogen peroxide. The titrating solution was prepared by dissolving 1 ml of potassium permanganate acidified with sulfuric acid.

TABLE 1

| Sample | Emulsifier | Color Change Time (in seconds) |
| --- | --- | --- |
| A | Sodium carboxymethyl Cellulose | 0.15 |
| B | Xanthan Gum | 0.12 |
| C | Carbopol 974P-NF | 0.55 |
| D | Polyvinylpyrrrolidone | 0.65 |
| E | Guar Gum | 0.18 |
| F | Polyethacrylate | 0.62 |

TABLE 1-continued

| Sample | Emulsifier | Color Change Time (in seconds) |
| --- | --- | --- |
| G | Poloxamer | 0.58 |
| H | Polyethylene Glycol | 0.32 |
| I | Acrylates/Ammonium Methacrylate Copolymer | 0.68 |
| J | Ammonium Styrene/Acrylates Copolymer | 0.72 |
| K | Acrylic Emulsion (proprietary) | 0.81 |
| L | Hydroxyethyl Cellulose | 0.22 |

The above table indicates that Samples C,D,F,G,H,I, J and K comprising [ICP(SI)] emulsifiers are substantially more suitable to be employed in delaying solubility of the emulsified carbamide peroxide when used as a method of delivering bleaching actives to plaque-free tooth enamel surfaces. There are several advantages of this type of emulsifiers over traditional toothpaste thickening agents. One of the most significant advantage is that the saliva solubility of [ICP(SI)] emulsed carbamide peroxide is delayed sufficiently to allow the removal of the enamel surface plaque formation by the abrasive agents prior to the onset of the bleaching activity. The results of this study are reflected in FIGS. 1 and 2.

The emulsifiers in samples A,B,E, and L dissolve more readily to activate the carbamide peroxide at a much faster rate and thus exhaust the available carbamide peroxide before the cessation of the 2 minute toothbrushing procedure. The average time to dissolve the emulsifier in those samples is approximately 20 seconds and the average time to dissolve the [ICP(SI)] emulsifier is approximately 60 seconds. This is shown graphically in FIG. 1 where the solid line indicates the dissolution of the [ICP(SI)] emulsifying polymer. It is the duration of the delaying action of the invention. The broken line illustrates the dissolution of the commonly used thickening and emulsifying agent in toothpaste employed today.

Figure 2:
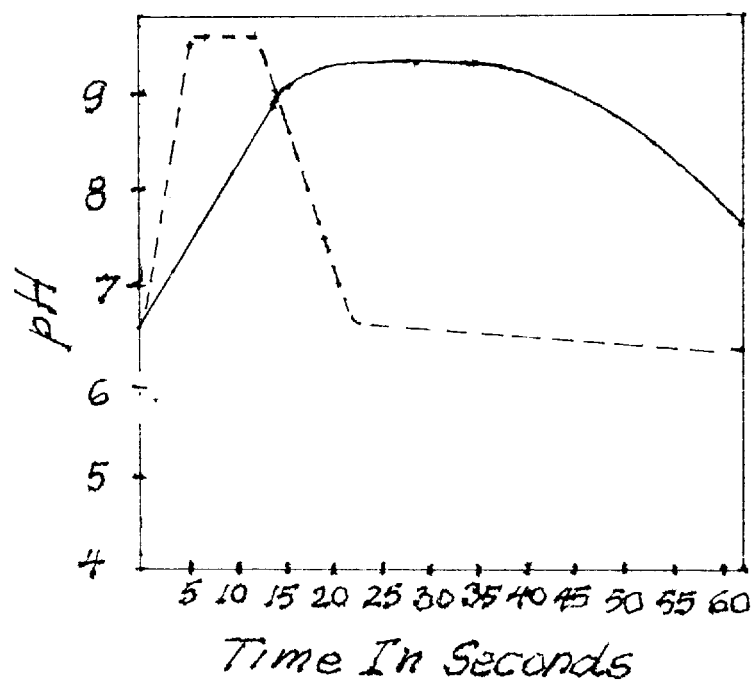
FIG. 2 depicts a graph showing the pH of the composition of the present invention in use.

The above study can be appreciated more easily by reference to FIG. 2 wherein the acid-base neutralization of the present invention is apparent. All samples were neutralized to a pH between 6–6.5 using 10% sodium hydroxide. At base line there is relative chemical inactivity of 2–4 seconds and then the samples emulsed in usual emulsifiers, illustrated by the broken line, increase the pH value more rapidly thereby activating the peroxide more quickly and then level off at pH 6.8 for the duration. The pH of 6.8 is relatively weak to produce satisfactory bleaching. However, [ICP(SI)] emulsed samples of the present invention start at the same pH at the base line and dissolve at a slower and more predictable rate and maintain relatively high pH at 60 seconds where it remains for most of the 2 minutes that is required for toothbrushing procedure and better remain for most of the 2 minutes that is required for toothbrushing procedure and better oral hygiene. This delay in activation of the bleaching active allows the abrasive agents to remove the surface plaque and thus facilitate carbamide peroxide to diffuse freely into the plaque-free enamel to effect bleaching.

EXAMPLES

In order to point out more fully the nature of the present invention, the following specific examples are given as an illustrative embodiment of the present compositions, processes and methods produced thereby.

Example 1

(A) In 50 grams purified water, 1.5 grams of emulsifier Carbopol 934/Polyvinyl pyrrolidone in 75:25 ratio are added and dissolved with gradual stirring. To the mixture 20 ml of hydrogen peroxide (50%) were added and mixed for additional 5–10 minutes. The acid composition was then adjusted between pH 5.5 and 6.5 with 10% NaOH. The composition thickens to a gel and set aside.

(B) In a separate vessel 210 grams of Methyl Methacrylate Crosspolymer GMX-0610 obtained from Perspere Corp. was added.

(C) In another separate vessel continuous phase of the invention was prepared comprising the following ingredients:

| | Weight % |
|---|---|
| Sodium fluoride | 1.05 |
| Propylene glycol | 24.10 |
| Sodium lauryl sulfate | 5.04 |
| Water | 43.40 |
| Vinyl pyrrolidone/Acrylic acid* | 1.02 |
| Hydroxyethyl cellulose | 2.01 |
| Glycerin | 18.85 |
| Sodium saccharine | 0.47 |
| Flavor | 2.76 |
| Sodium benzoate | 0.55 |
| Benzoic acid | 0.06 |
| Sodium EDTA | 0.14 |
| Sodium hydroxide (10% solution) | 0.55 |

*Dry blend copolymer containing 25% vinyl pyrrolidone and 75% Carbopol. The vinyl pyrrolidone in the mixture delays the solubility of the emulsion further than Carbopol alone.

After the bleaching composition (A) has been prepared to desired consistency, 50 grams of this composition is added to 50 grams of the water insoluble abrasive suspension (B) and the intimate mixture of the two immiscible phases are dispersed in each other and then, with the aid of the colloidal mill, agitated until extremely fine homogeneous dispersion is obtained. 100 grams of the dispersion so obtained was then added to 50 grams of the continuous phase (C) and the two phases mixed in a colloidal mill and the resultant composition comprised the discontinuous phases (A) dispersed homogenously throughout the continuous phase (B) and (C) of the present invention. The final formulation was as follows:

| | Weight % |
|---|---|
| Water, purified | 15.75 |
| Methyl Methacrylate Crosspolymer GMX-0610 | 53.71 |
| Hydrogen peroxide | 10.00 |
| Carbopol 934 | 0.37 |
| Hydroxyethyl cellulose | 0.73 |
| Sodium fluoride | 0.38 |
| | (0.17% F ions) |
| Sodium lauryl sulfate | 1.83 |
| Propylene glycol | 8.75 |
| Glycerin | 6.84 |
| Sodium saccharine | 0.17 |
| Sodium benzoate | 0.20 |
| Benzoic acid | 0.02 |
| Sodium EDTA | 0.05 |
| Flavor | 1.00 |
| Sodium hydroxide (10%) q.s. pH 6.5 | 0.20 |

Carbopol in this composition sufficiently retards the dissolution of the emulsed hydrogen peroxide to allow the abrasive agent Methyl Methacrylate Crosspolymer GMX-0610 to remove the dental plaque and pellicles from the enamel surface and thus allow the bleaching active hydrogen peroxide to diffuse through the plaque-free enamel with ease.

Example 2

Example 1 was repeated except that in phase (A) to 50 grams of deionized water 28 grams of carbamide peroxide in addition to 20 ml of hydrogen peroxide was added to the composition with constant stirring in the same manner as in Example 1.

The advantage of having carbamide peroxide in this example is that it provides excellent quick dissolution and onset of bleaching activity due to its higher pH level than that provided by hydrogen peroxide. Carbamide peroxide when dissolved breaks down into hydrogen peroxide and urea which is an ammonium compound that is highly alkaline. The final composition of this example is as follows:

| | Weight % |
|---|---|
| Water | 13.75 |
| Sodium fluoride | 0.38 |
| Hydrogen peroxide (50%) | 5.00 |
| Carbamide peroxide | 7.00 |
| Methyl methacrylate crosspolymer GMX-0610 | 53.71 |
| Acylin 44* | 0.37 |
| Hydroxyethyl cellulose | 0.73 |
| Sodium lauryl sulfate | 1.83 |
| Propylene glycol | 8.75 |
| Glycerol | 6.84 |
| Sodium saccharine | 0.17 |
| Sodium benzoate | 0.20 |
| Benzoic acid | 0.02 |
| Flavor | 1.00 |
| Sodium EDTA | 0.05 |
| Sodium hydroxide (10%) q.s. pH 6.5 | 0.20 |

*Acylin 44 is a modified Polyethylene Glycol/Propylene Glycol Copolymers obtained from ISP Technologies, Inc. It renders decreased water and saliva solubility of the bleaching agents carbamide peroxide and hydrogen peroxide for approximately 1 minutes to allow the abrasive agent to remove the plaque accumulations from the tooth surfaces.

Example 3

A bleaching oral composition in dentifrice form was formulatated containing the carbamide peroxide in colored stripe gel form and hydrogen peroxide in the main body of the toothpaste as described in U.S. Pat. No. 3,980,767, Chown et al. The composition is as follows

| | Weight % |
|---|---|
| (A) Gel Composition | |
| Sodium fluoride | 0.32 |
| | (0.14 (w/v fluoride ion) |
| Carbopol 974 P-NF | 1.25 |
| Sorbitol (70% soln) | 10.00 |
| Glycerin | 10.00 |
| Carbamide peroxide | 14.00 |
| Sodium lauryl sulfate | 1.50 |
| Sodium saccharine | 0.20 |
| Flavor | 1.25 |
| FD&C Yellow 5 | 0.15 |
| FD&C Red 40 | 0.05 |
| Water, purified | 29.60 |
| (B) Paste Composition | |
| Sodium fluoride | 0.32 |
| Hydrogen peroxide (50% solution) | 10.00 |

-continued

|  | Weight % |
|---|---|
| Carbopol 943 | 0.51 |
| Sorbitol (70% soln) | 5.18 |
| Glycerin | 5.18 |
| Sodium lauryl sulfate | 1.50 |
| Sodium saccharine | 0.20 |
| Flavor | 1.25 |
| Polytetrafluoroethylene (Teflon) | 52.00 |
| Water, purified | 29.86 |

Both phases were neutralized to a pH of about 5.5 and 6.5 with freshly prepared 10% sodium hydroxide and the stripe composition to the main composition is approximately 15:100

The above hydrogen peroxide/carbamide peroxide blend composition is very effective and stable when used topically for bleaching tooth surfaces. When extruded from the tube container the gel composition will be in the form of one or more stripes enclosed in the periphery of the toothpaste surrounded by the paste composition. The gel and the paste composition must be sufficiently of heavy viscosities to prevent migration (bleeding) of the colored gel into the white paste composition. As in Example 1 and Example 2 this composition was very stable even at storage at 35° C. for at least 12 months. There was no observable deterioration or "bleeding" of either composition at the end of the storage period.

Example 4

A bleaching/antimicrobial dentifrice composition of the present invention was made consisting of the following ingredients:

|  | Weight % |
|---|---|
| Hydrogen peroxide (50%) | 10.00 |
| Carbamide peroxide | 14.00 |
| Sodium fluoride | 0.38 |
| Pecogel S-2120* | 0.50 |
| Hydroxyethyl cellulose | 0.50 |
| Triethanolamine | 0.30 |
| Water, purified | 10.00 |
| Glycerin | 10.75 |
| Tetrafluoroethylene (Teflon)** | 50.58 |
| Sodium lauryl sulfate | 1.25 |
| Sodium saccharine | 0.18 |
| Sodium citrate | 0.20 |
| Citric acid | 0.20 |
| Triclosan | 0.06 |
| Flavor | 1.10 |

*VP/Dimethicolylacrylate is a inclusion complex polymer to retard the solubility of emulsified bleaching actives. It is obtained from Phoenix Chemical, Inc.
**Polytetrafluoroethylene (tradenames and synonyms Teflon and Zonyl) was obtained from DuPont Fluoroproducts, Willmington, DE. It is a highly stable thermoplastic homopolymer composed of at least 20,000 C2F4 monomer units linked into very long unbranched chain. It is very inert chemically and is not affected in acid, alkaline, oxydizing and reducing agents unless boiled at higher than 400 degrees C.

Triethanolamine was used to thicken the composition by neutralizing the pH to about 6.2 and 6.5.

The combination of the above noted ingredients form an effective and stable dentifrice past composition which provides antimicrobial protection in the prevention and control of periodontal (gum) disease; aids in the reduction of tooth decay; provides an oxygenating cleansing action on the oral soft tissues; provides sustained release of bleaching on the tooth surfaces when topically applied on the tooth surfaces on regular daily basis.

The composition has 5% composition of hydrogen peroxide/carbamide peroxide blend.

Example 5

A peroxygen/anesthetic tablet composition of the present invention for treatment of post-extraction septic socket was made containing the following ingredients:

|  | Weight % |
|---|---|
| Carbamide peroxide | 28.00 |
| Pluronic F 127 | 18.00 |
| Avicel PH200 MCC* | 16.00 |
| Polyvinylpyrrolidone | 18.00 |
| Sorbitol (70% solution) | 8.55 |
| Sodium saccharine | 0.20 |
| Benzocaine | 10.00 |
| Flavor | 1.25 |

Microcrystalline cellulose obtained from FMC Corp., Philadelphia, Pa.

Dry ingredients carbamide peroxide, Pluronic F 127, Avicel PH200 MCC, Polyvinylpyrrolidone, sodium saccharine and Benzocaine were blended in a laboratory spatula blender and then Sorbitol was added to moisten, but not dissolve, the admixture. Ten (10) grams of the dry mixture was poured into compression tablet punch press having hollow center. The core rod having the same outer dimension as the inner diameter of the hollow center was then positioned into the said hollow center and the upper punch electronically activated to compress the dry mixture into a single core tablet.

The tablets were then clinically tested using trial subjects that had their lower third molars, either left or right, extracted and demonstrated clinical manifestation of post-extraction septic socket associated with bleeding and pain. One 10 gram conical tablet was inserted into the necrotizing socket and the patient was observed. After 5 minutes, the pain subsided and the bleeding decreased significantly. The patients were then given tablets to take home and to insert one tablet 3 times daily for 3 days when they returned for clinical examination. There was no evidence of post-extraction bleeding nor any signs of infection as would be evidenced with pus formation. The patients reported no pain in the last 3 days.

Example 6

Example 1 was repeated except the abrasive agent Methyl Methacrylate Crosspolymer GMX-0610 was substituted with Polyethylene powder. This example was found to be equally effective in the process of plaque removing and bleaching of the dental enamel and dentin.

Example 7

A dental composition for bleaching, plaque removing and in the control, prevention and treatment of gingivitis was prepared in accordance with the present improved comprising the following ranges and groups of ingredients:

|  | Weight % |
|---|---|
| Water, purified | 0.50–82.00 |
| Hydrogen peroxide | 1.00–45.00 |
| Carbamide peroxide | 3.00–50.00 |
| Abrasive(polymer, copolymer, crosspolymer) | 10.00–75.00 |

-continued

|  | Weight % |
|---|---|
| Thickeners and emulsifiers | 0.50–15.00 |
| Fluorides | 0.00–5.00 |
| Foaming agent | 0.05–10.00 |
| Humectants | 0.50–45.00 |
| Sweeteners | 0.05–2.50 |
| Flavors | 0.50–20.00 |
| Preservatives | 0.50–5.00 |
| Colors | 0.00–5.00 |
| Antimicrobials | 0.00–5.00 |
| Anesthetics, topical | 0.00–15.00 |
| Acids and/or Alkalies | q.s. pH 5.5–14.0 |

Example 8

A bleaching/antimicrobial/anti-plaque mouthwash composition in accordance with the present invention was prepared containing the following ingredients:

|  | Weight % |
|---|---|
| Hydrogen peroxide (50%) | 6.00 |
| Carbamide peroxide | 9.00 |
| Water, purified | 42.06 |
| Glycerin | 12.00 |
| Sorbitol (70% soln) | 14.00 |
| Alcohol | 7.75 |
| Benzoic acid | 1.05 |
| Flavor | 0.80 |
| Sodium benzoate | 0.40 |
| Poloxamer 407 | 0.75 |
| Cellulose crosspolymer | 5.65 |
| Triclosan | 0.03 |
| FD&C Red 40 | 0.01 |

Example 9

A bleaching/antimicrobial/anti-gingivitis mouthwash composition in accordance with the present invention was prepared containing the following ingredients:

|  | Weight % |
|---|---|
| Hydrogen peroxide, emulsed | 3.00 |
| Carbamide peroxide, emulsed | 9.00 |
| Eucalyptol | 0.092 |
| Thymol | 0.064 |
| Methyl salycilate | 0.060 |
| Menthol | 0.042 |
| Water, purified | 41.93 |
| Alcohol | 8.60 |
| Flavor | 1.75 |
| Poloxamer | 1.00 |
| Sorbitol (70%) | 16.75 |
| Sodium saccharine | 0.40 |
| Sodium lauryl sulfate | 1.00 |
| Benzoic acid | 0.35 |
| Sodium benzoate | 0.30 |
| Polyvinylparrolidone/Polyethylene Oxide copolymer | 11.00 |

The bleaching/antimicrobial/anti-gingivitis mouthwash of this example was found to be effective in the process of bacteriocidal action upon the reduction of bacterial oral colonies prior to the bleaching actives being effective in the whitening of the tooth surface enamel. The copolymer polyvinylpyrrolidone/Polyethylene Oxide is also efficacious in retaining the hydrogen peroxide actives in contact with the enamel for approximately 12 hours after completion of the prophylaxis procedure.

Example 10

A bleaching/antimicrobial dentifrice prophylaxis paste was made containing the following ingredients:

|  | Weight % |
|---|---|
| Carbamide peroxide (Urea peroxide) | 14.00 |
| Hydrogen peroxide (50%) | 10.00 |
| Sodium fluoride | 0.38 |
| Carbopol 943 | 1.50 |
| Glycerine | 10.00 |
| Sodium saccharine | 0.20 |
| Methyl paraben | 0.20 |
| Propyl Paraben | 0.15 |
| Polyethylene powder, 150 micron size | 48.00 |
| Water | 14.54 |
| Flavor | 1.00 |
| Triclosan | 0.03 |

To thicken the composition Sodium Hydroxide (10%) was used to neutralize the acrylic polymer Carbopol 943 to a pH between 6.2 and 6.8. The abrasive ness of the polyethylene powder polymer was found to be effective in the plaque removal when used as a prophylaxis paste.

Example 11

An oxygenating/antimocrobial/emollient cleansing shower and bathtub spray was prepared in accordance with the present invention containing the following ingredients:

|  | Weight % |
|---|---|
| Hydrogen Peroxide (50) | 6.00 |
| Carbamide Peroxide | 14.00 |
| Alcohol | 10.50 |
| Triclosan | 0.73 |
| Sodium Laurate Sulfate (and) Soyamidopropyl Betaine (and) Cocamide DEA (and) Glycol Stearate (and) PropyleneGlycol | 20.00 |
| Dimethiconol | 2.00 |
| Sodium Chloride | 0.40 |
| Polymethoxy Bicyclic Oxazolidine | 0.40 |
| Fragrance | 1.50 |
| Citric Acid | 0.20 |
| Sodium Citrate | 0.20 |
| Water | 44.07 |

This composition contained 3% of active Hydrogen Peroxide/Carbamide Peroxide blend. When used as a spray after shower or bath the oxygenating peroxygen agents prevent formation of molds and fungi while Triclosan destroys the residual bacterial colonies. The emulsifiers Sodium Laurate Sulfate (and) Soyamidopropyl Betaine (and) Cocamide DEA (and) Glycol Stearate (and) Propylene Glycol emulsify the soap deposits which are then dissolved by the alcohol and removed by Dimethiconol by evaporation.

Example 12

A stable sustained release oxygenating/antimicrobial/soothing shaving gel was formed containing the following ingredients:

|  | Weight % |
|---|---|
| Phase A |  |
| Emulsed Hydrogen Peroxide/Carbamide Peroxide (and) Carbopol | 20.00 |
| Triclosan | 0.75 |
| Phase B |  |
| Water, purified | 33.65 |
| Glycerin | 2.00 |
| Phase C |  |
| TEA Lauryl Sulfate | 12.50 |
| Sodium Laurath Sulfate | 12.50 |
| Cocamidopropyl Betaine | 6.00 |
| Phase D |  |
| PEG-150 Penterythrityl Testracearate | 2.00 |
| Phase E |  |
| PEG-60 Lauramide DEAHydrogenated Castor Oil | 2.00 |
| Lauramide DEA | 2.00 |
| Phase F |  |
| Fragrance | 0.85 |
| Phase G |  |
| Water, Butylene Glycol, Oat Extract | 1.50 |
| Betaglucan | 3.00 |

The shaving gel preparation was prepared by combining Phase A and Phase B and heat to 65° C. using a sweep blade mixer at low speed. Phase C ingredients were added in that order to Phase B maintaining the 65° C. temperature. The ingredient in Phase D was heated until it is a clear liquid and then added to batch until uniform and clear. When clear the batch was cooled to 45° C. Phase E ingredients were combined and heated to 50° C. and mixed slowly until the composition is clear. Then Phase F was added to Phase E and mixed until uniform. Phases E/F were added to the mixing Phases B/C/D/with continuous mixing with the addition of Phase A. Items in Phase G were combined and mixed until uniform before they were added to the batch. The final batch was then slowly mixed until clear and homogeneous.

This sustained release oxygenating/antimicrobial shaving gel is an excellent composition to be used topically on the shaved facial, underarm and leg surfaces to aid in the healing of the irritated areas and accidental cuts and abrasions that may occur during the procedure. The emulsified oxygenating agents will form a long lasting thin protective film on shaved surfaces. It has a oxygenating concentration of 3%.

Example 13

An oxygenating/soothing/antibacterial after shave lotion was prepared in accordance with the present invention containing the following ingredients:

|  | Weight % |
|---|---|
| Phase A |  |
| Emulsed Hydrogen Peroxide/Carbamide Peroxide with Carbopol | 10.00 |
| Phase B |  |
| Water | 44.40 |
| SD Alcohol 40 | 12.00 |
| Sodium Lactate | 6.27 |
| Phase C |  |
| Propylene Glycol | 4.33 |
| Aloe Barbadensis Gel | 20.50 |
| Methylparaben | 0.30 |
| Propylparaben | 0.20 |
| Disodium EDTA | 0.50 |
| Fragrance | 1.50 |

Example 14

A prototype oxygenating/antimicrobial antiperspirant stick was prepared containing:

|  |  |
|---|---|
| Hydrogen Peroxide | 5.00 |
| Carbamide Peroxide | 7.77 |
| Polyvinylpyrrolidone | 8.50 |
| Hydroxyethyl Cellulose | 1.50 |
| Triclosan | 0.50 |
| Cyclomethicone | 33.08 |
| Stearyl Alcohol | 16.00 |
| Castor Wax | 4.00 |
| PEG-8 Distearate and Water | 4.00 |
| Aluminum-Zirconium Tetrachloroxydrex-GLY Powder | 18.15 |
| Fragrance | 1.50 |

Thus, there has been described a unique and novel dental bleaching composition comprising an effective amount of one or more hydrophobic bleach-stable solid, inert abrasive agents that are polymers, copolymers and crosspolymers dispersed in a hydrophilic continuous phase comprising emulsed bleaching actives in a reduced water and saliva solubility hydrophilic inclusion complex polymer or copolymer said bleaching actives being distributed, dissolved or otherwise incorporated into a hydrophilic continuous phase consisting of sweeteners, flavors, humectants, topical anesthetics, preservatives, alcohols, fluorides, and other desired formulating agents the said bleach-stable solid, inert, hydrophobic abrasive when mixed with the continuous hydrophilic phase will form a homogeneously dispersed discontinuous phase throughout the final composition which is then packaged in a single tube or chamber to be used topically for removal of plaque by mild abrasive action on tooth surfaces prior to bleaching.

The invention also provides a method and process for making such bleaching and whitening composition for topical application in the oral cavity for selectively removing dental plaque formations from enamel surfaces prior to, or contemporaneous with, the bleaching action.

The invention further provides a method and process for making a bleaching composition for topical application in the oral cavity for selective retardation of the bleaching action comprising a hydrophobic discontinuous phase comprising solid inert polymers, copolymers and crosspolymers of sufficient particle size, approximately between about 4 microns and 150 microns, to affect mild action on the enamel surfaces during the process of plaque removal prior to the onset of the bleaching action, dispersed homogeneously throughout a continuous phase of water soluble, a water miscible, hydrophilic phase comprising bleaching actives emulsified in an inclusion complex polymer or copolymer suspended, distributed, dissolved or otherwise incorporated throughout the continuous phase which may contain additional bleach-stable formulating agents such as sweeteners, flavors, preservatives, fluoride yielding compounds, alcohols, humectants and similar substances, the said emulsified bleaching actives are rendered substantially less water soluble when effectively applied in the oral cavity for bleaching or whitening of tooth surfaces and thereby fulfills all the objects and advantages sought for plaque removal prior to bleaching of tooth surfaces.

It should be understood that changes and modifications including the substitution, elimination or addition of various components can be made in the subject bleaching composition, or the method of making such compositions, without departing from the nature and principle of the invention. Therefore, all such changes and modifications which do not depart from the nature and principle of the invention are deemed to be covered by the invention which is limited only by the claims.

While particular embodiments of the present invention have been illustrated and described, it will be obvious to those skilled in the art that various changes and modifications may be made without departing from the spirit and scope of the invention, and it is intended to cover in the appended claims all such modifications that are within the scope of the invention.

What is claimed is:

1. A composition for bleaching and removing plaque from tooth surfaces, which is activated by contact with saliva following application to an oral cavity, comprising:
   1) a homogenous dispersion comprising
      a) a discontinuous hydrophobic phase containing inert, solid, bleach-stable abrasive polymeric particles having a particle size of between approximately 4 and 150 microns; and
      b) a continuous hydrophilic phase comprising a peroxide bleaching agent selected from the group consisting of hydrogen peroxide, carbamide peroxide, and mixtures thereof, emulsified in a bleach-stable inclusion complex polymer, wherein said inclusion complex polymer reduces the water-solubility of said bleaching agent, and
   2) at least one member selected from the group consisting of a fluoride-yielding compound, a sweetening or other flavoring agent, a preservative, a humectant, and a topical anesthetic.

2. The composition of claim 1, wherein said bleaching agent is hydrogen peroxide or carbamide peroxide.

3. The composition of claim 1, comprising at least one member selected from the group consisting of a) 0.5 to 10 percent by weight, based on the total weight of the composition, of a sweetening agent; b) 0.5 to 15 percent by weight, based on the total weight of the composition, of a preservative; c) up to 15 percent by weight, based on the total weight of the composition, of a topical anesthetic; d) 1.0 to 25 percent by weight, based on the total weight of the composition, of a thickening agent or additional emulsifying agent; e) 0.5 to 45 percent by weight, based on the total weight of the composition, of a humectant; f) a buffer to adjust the pH of the composition to between 5.5 and 8.5; g) up to 25 percent by weight, based on the total weight of the composition, of an alcohol; h) up to 15 percent by weight, based on the total weight of the composition, of a colorant; i) up to 50 percent by weight, based on the total weight of the composition, of a solvent other than water; j) up to 5 percent by weight, based on the total weight of the composition, of a fluoride-yielding compound; and k) 10 to 80 percent by weight, based on the total weight of the composition, of water.

4. The composition of claim 2, comprising about 1 percent to 45 percent by weight, based on the total weight of the composition, of hydrogen peroxide.

5. The composition of claim 4, comprising about 2 to 25 percent hydrogen peroxide.

6. The composition of claim 2, comprising about 3 to 55 percent by weight, based on the total weight of the composition, of carbamide peroxide.

7. The composition of claim 6, comprising about 5 to 45 percent carbamide peroxide.

8. The composition of claim 1, wherein said abrasive polymeric particles comprise a polymer selected from the group consisting of polymethyl-methacrylate, crosslinked methylmethacrylate-ethyleneglycoldimethacrylate, ethylacrylate-methacrylate copolymer, polycellulose acetate, polycellulose nitrate, poly(phenyl-formaldehyde), polytetrafluoroethylene, polyethylene, and polyvinylpyrollidone/dimethylaminoethylmethacrylate/polycarbamyl polyglcyol ester.

9. The composition of claim 8, wherein said abrasive polymeric particles are present in an amount of about 10 to 75 percent by weight, based on the total weight of the composition.

10. The composition of claim 1, wherein said inclusion complex polymer is selected from the group consisting of anionic, cationic and amphoteric polymers; alkanolamides, amineoxides, ethoxylated fatty esters, polyol block copolymers; ethoxylated alcohols, ethoxylated sorbitan esters, silicones, polyethylene glycols, polypropylene glycols, acrylic polymers and polyvinylpyrollidone.

11. The composition of claim 10, wherein said inclusion complex polymer is selected from the group consisting of ammonium-styrene/acrylate copolymers, ammonium-methacrylate/acrylate copolymers, polyethacrylate, polyol block copolymers, and polyvinylpyrollidone.

12. The composition of claim 10, wherein said inclusion complex polymer is present in an amount of from about 0.5% to 45% by weight with respect to the total weight of the composition.

13. The composition of claim 1, which further includes one member selected from the group consisting of of an alkali, foaming agent, antimicrobial agent or water.

14. The composition of claim 1, wherein said topical anesthetic is selected from the group consisting of ethyl 4-aminobenzoate, chlorobutanol, lidocain, butacaine sulfate, tetracaine hydrochloride, dyclonine hydrochloride, cocaine hydrochloride and mixtures thereof.

15. The composition of claim 1, wherein said topical anesthetic is present in an amount of up to about 15% by weight with respect to the total weight of the composition.

16. The composition of claim 1, wherein said sweetening agent is selected from the group consisting of sodium saccharine, xylitol, sorbitol, and mixtures thereof.

17. The composition of claim 1, wherein said sweetening agent is present in an amount of from about 0.05% to 2.5% by weight with respect to the total weight of the composition.

18. The composition of claim 1, wherein said flavoring agent includes at least one member selected from the group consisting of anise oil, clove oil, peppermint oil, spearmint oil, menthol, methyl salicylate, blackberry, strawberry, chocolate, vanilla, cherry, grape, lime, lemon, mint, and mixtures thereof.

19. The composition of claim 1, wherein said flavoring agent is present in an amount of from from about 0.5% to 20% by weight with respect to the total weight of the composition.

20. The composition of claim 1, wherein said preservative is selected from the group consisting of sodium benzoate, methyl paraben, propyl paraben, phenyl mercuric nitrate, sodium bisulfite, disodium calcium EDTA, chlorobutanol, and mixtures thereof.

21. The composition of claim 1, wherein said preservative is present in an amount of from about 0.5% to 5.0% by weight with respect to the total weight of the composition.

22. The composition of claim 1, which is capable of forming a film on a tooth surface.

23. A method of bleaching teeth, comprising the steps of:
(a) forming a bleaching composition as defined in claim 1 into gel, paste or tablet form; and
(b) introducing said bleaching composition onto tooth surfaces.

* * * * *